Aug. 30, 1960 M. TANTAU Plant Pat. 1,969
ROSE PLANT
Filed Nov. 18, 1959
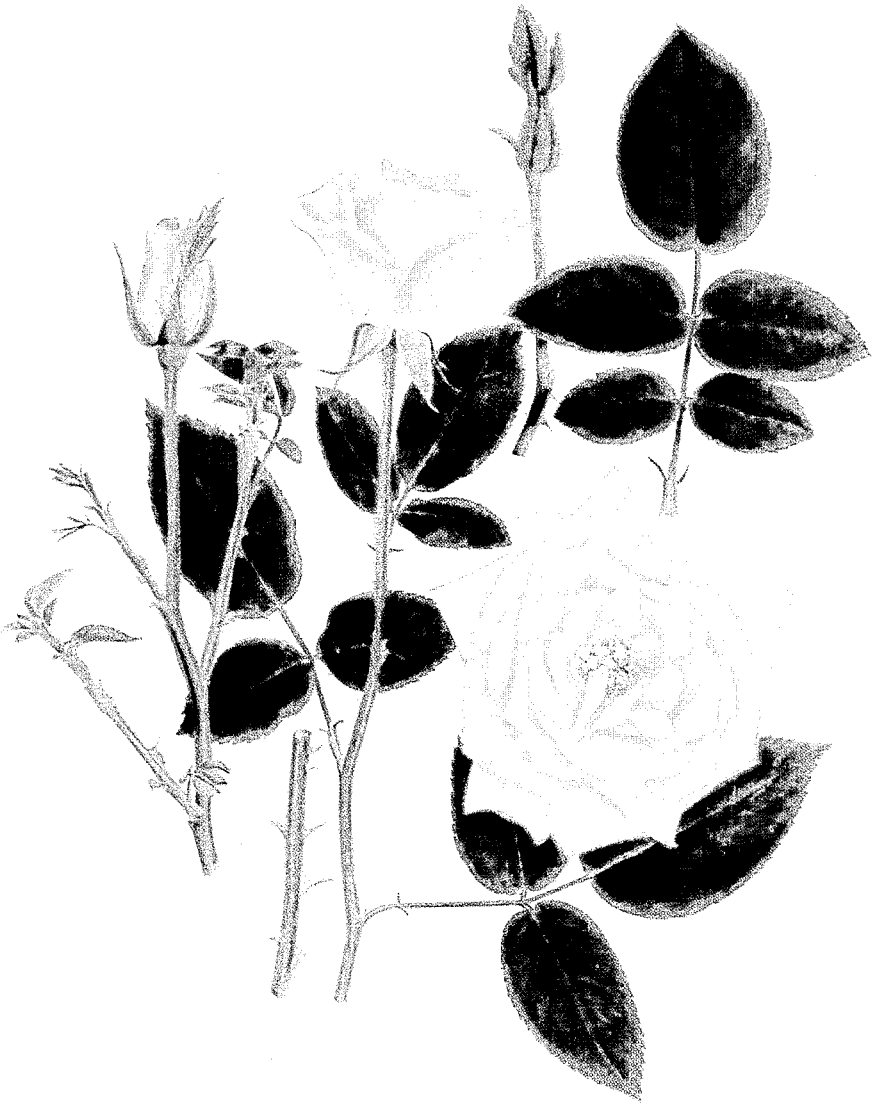
Inventor.
Mathias Tantau
By Robb & Robb
Attorneys United States Patent Office Plant Pat. 1,969
Patented Aug. 30, 1960

1,969

ROSE PLANT

Mathias Tantau, Uetersen, Holstein, Germany, assignor to Jackson & Perkins Company, Newark, N.Y., a corporation of New York Filed Nov. 18, 1959, Ser. No. 853,986

1 Claim. (Cl. 47—61)

The present invention relates to a new and distinct variety of rose plant of the large-flowered hybrid floribunda (grandiflora) class, which was originated by me by crossing an unnamed and unpatented seedling derived from a cross of an unnamed and unpatented seedling × "Peace" (U.S. Plant Patent No. 591), with another unnamed and unpatented seedling derived from a cross of an unnamed and unpatented seedling × "Alpine Glow" (U.S. Plant No. 1,395).

The primary objective of this breeding was to produce a new rose variety characterized by a freer flowering habit than that of the usual older hybrid tea roses, one of which was used as one of the antecedents of my new variety, particularly because it was especially characterized by better than average resistance to diseases and better than average winter hardiness. These objectives were fully achieved, along with other desirable improvements, as evidenced by the following unique combination of characteristics which are outstanding in the new variety, and differentiate it from its parents as well as from all other varieties of which I am aware:

(1) Good winter hardiness;

(2) An unusual foliage arrangement of the first three leaves beneath the buds, these leaves each having only three leaflets;

(3) A free-flowering habit;

(4) Branched sepals which are long and appear above the early stage of the buds;

(5) A distinctive petal shape characterized by the tips of the petals all bending back as soon as the flower is released from its sepal;

(6) A distinctive Peach Red general color tonality of the flowers, lightly overcast with Scarlet; and (7) Unusually long lasting qualities of the flowers.

Asexual reproduction of the new variety as performed on my behalf at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonable to make the same in a color illustration of this character.

The following is a detailed description of the new variety, with color terminology in accordance with Ridgway's Color Standards and Nomenclature:

Parentage: Seedling.

*Seed parent.*—An unnamed seedling derived from another unnamed seedling × "Peace."

*Pollen parent.*—An unnamed seedling derived from another unnamed seedling × "Alpine Glow."

Classification:

*Botanic.*—Large-flowered hybrid floribunda.

*Commercial.*—Grandiflora.

*Flower*

(Observations made from specimens grown in a greenhouse at Newark, New York, U.S.A., in the early afternoon during the early part of March.)

Blooming habit: Recurrent—continuous.

Bud:

*Size.*—Large.

*Form.*—Pointed; is not affected by wet or hot weather.

*Color.*—When sepals first divide—Spectrum Red, Plate 1. When petals begin to unfurl—Scarlet-Red, Plate 1. When half-blown: inside of petals—Scarlet, Plate 1, overcast with Grenadine Red, Plate 2; reverse of petals—Scarlet, Plate 1.

*Sepals.*—Branched; with "hood" above bud; curl back when petals begin to unfurl. Color: inside—Light Lumiere Green, Plate 17; outside—Light Bice Green, Plate 17.

*Calyx.*—Color—Absinthe Green, Plate 31. Shape—funnel. Size—Slender. Aspect—Smooth. Odor when rubbed—none.

*Peduncle.* — Length — medium. Aspect — rough. Strength—erect; slender. Color—Lettuce Green, Plate 5.

*Opening.*—Opens up well; is not affected by adverse weather conditions.

*Size.*—Large. Average size when fully expanded—from 4½" to 5".

*Borne.*—Both singly and several together.

*Stems.*—Long; strong.

*Form (when first open).*—Cupped. Permanence—retains its form to the end.

*Petalage.*—Double (full but open center). Number of petals under normal conditions—from 30 to 35.

*Color.*—Center of flower—Scarlet, Plate 1, lightly overcast with Peach Red, Plate 1. Outer petals—Strawberry Pink, Plate 1, lightly overcast with Eosine Pink, Plate 1. Base of petals (aiglet)—Buff Yellow, Plate 4. Inside of petals—Peach Red, Plate 1, lightly overcast with Scarlet, Plate 1. Reverse of petals—Peach Red, Plate 1. General tonality from a distance—Peach Red, Plate 1, lightly overcast with Scarlet, Plate 1.

*Discoloration.*—General tonality at end of first day—Peach Red, Plate 1, lightly overcast with Scarlet, Plate 1. Second day—Peach Red, Plate 1, lightly overcast with Scarlet, Plate 1. Third day—Peach Red, Plate 1.

Petals:

*Texture.*—Thick; is not affected by wet or hot weather.

*Appearance.*—Inside—satiny. Outside—shiny.

*Form.*—Oval; slightly notched; with tips of petals bent back.

*Arrangement.* — Imbricated (regularly arranged shingle-like).

*Petaloids in center.*—Few; large.

*Persistence.*—Drop off cleanly.

*Fragrance.*—Strong. Nature—fruity (russet apple).

*Lasting quality.*—On the plant—very long. As cut flower—very long.

*Genital organs*

Stamens, anthers: Small; many; regularly arranged around styles. Color—Capucine Yellow, Plate 30.

Stamens, filaments (threads): Medium length. Color—Persian Lilac, Plate 38.

Pollen: Color—Ivory Yellow, Plate 30.

Styles: Bunched; uneven length; medium length; thin.

Stigmas: Color—Light Chalcedony Yellow, Plate 17.

Ovaries: All enclosed in calyx.
Hips: None.
Seeds: None.

*Plant*

Form: Bush.
Growth: Vigorous; upright.
Foliage: Compound of 3 to 5 leaflets; top 3 leaves have 3 leaflets each.
*Size.*—Large.
*Quantity.*—Normal.
*Color.*—New foliage: upper side—Rainette Green, Plate 31, overcast with Victoria Lake, Plate 12; under side—Van Dyke Red, Plate 13. Old foliage: upper side—Dark Cress Green, Plate 31; under side—Light Bice Green, Plate 17.
*Shape.*—Oval pointed.
*Texture.* — Upper side — leathery. Under side—smooth.
*Ribs and veins.*—Ordinary.
*Edge.*—Serrated (saw-toothed).
*Serration.*—Both double and single; small.
*Leaf stem.*—Color—Absinthe Green, Plate 31. Under side—prickly.
*Stipules.*—Medium length; bearded.

Wood:
*New wood.* — Color — Biscay Green, Plate 31. Bark—smooth.

*Old wood.*—Color—Cress Green, Plate 31. Bark—smooth.

Thorns:
*Thorns.*—Quantity: on main stalks from base—few; on laterals from stalk—ordinary. Form—narrow base; medium length; some straight and some hooked upward. Color (when young)—Pinkish Vinaceous, Plate 27. Position—irregular.
*Prickles.*—Quantity: on main stalks—none; on laterals—none.
*Short needles.*—Quantity: on main stalks—none; on laterals—none.

I claim:

A new and distinctive variety of rose plant of the large-flowered hybrid floribunda (grandiflora) class, substantially as herein shown and described, characterized particularly as to novelty by the unique combination of good winter hardiness, a distinctive foliage arrangement of the three leaves beneath each bud and consisting of only three leaflets each, a free-flowering habit, branched sepals, said sepals being long and appearing above the early stage of the bud, a distinctive petal shape, with the tips of the petals all bending back as soon as the flower is released from its sepal, a distinctive Peach Red, lightly overcast with Scarlet general color tonality of the flowers, and unusually prolonged lasting qualities of the flowers.

No references cited.

UNITED STATES PATENT OFFICE

CERTIFICATE OF CORRECTION

Plant Patent No. 1,969 August 30, 1960

Mathias Tantau

It is hereby certified that error appears in the printed specification of the above numbered patent requiring correction and that the said Letters Patent should read as corrected below.

Column 2, between lines 27 and 28, insert the topical word -- Bloom: --.

Signed and sealed this 11th day of April 1961.

(SEAL)
Attest:

ERNEST W. SWIDER
Attesting Officer

ARTHUR W. CROCKER
Acting Commissioner of Patents